United States Patent [19]
Shields

[11] Patent Number: 6,126,641
[45] Date of Patent: Oct. 3, 2000

[54] SHIELDED IV CATHETER INSERTION ASSEMBLIES

[76] Inventor: Jack W. Shields, 1950 Las Tunas Rd., Santa Barbara, Calif. 93103

[21] Appl. No.: 09/004,621

[22] Filed: Jan. 8, 1998

Related U.S. Application Data

[60] Provisional application No. 60/035,362, Jan. 10, 1997.

[51] Int. Cl.[7] .......................................... A61M 5/00
[52] U.S. Cl. ........................... 604/192; 604/162; 604/164
[58] Field of Search ..................... 604/192, 162, 604/163, 164, 158, 171

[56] References Cited

U.S. PATENT DOCUMENTS

| | | | |
|---|---|---|---|
| 4,917,669 | 4/1990 | Bonaldo | 604/164 |
| 5,007,901 | 4/1991 | Shields | 604/164 X |
| 5,401,250 | 3/1995 | Shields | 604/192 |

*Primary Examiner*—John D. Yasko

[57] ABSTRACT

I describe shielded intravenous (IV) catheter insertion assemblies wherein the catheter insertion needle hub, shank and leading bevel are safely shielded by wedge impaction inside conical holders resembling syringes after use for safely controlled insertion of an IV catheter having a leading taper, a tubular body and a trailing hub attachable to a Luer-Lok. An unfilled form of the assembly consists of a hollow cone whose leading frustal end resembles that of a standard 3.0 ml. syringe with a leading Luer-Lok for reversible attachment of a flanged needle hub on a soft catheter; and encloses a modified piston which enhances delicate control of the beveled needle tip in relation to the leading taper in the catheter. The open trailing apical end snugly admits passage through of a smaller bore syringe which reversibly slip connects to the catheter insertion needle hub and successively serves as a guide for the catheter insertion needle; a reliable means for assessing accuracy of insertion and flow at successive stages of insertion without shearing the catheter or producing venous injury after initial flashback of venous blood; and as a means for optionally obtaining an undiluted fresh blood sample. Upon retraction of the smaller bore syringe, the trailing apical end of the hollow cone provides a secure means for shielding the entire catheter insertion needle having a circular hub flange diameter greater than the external diameter of the snugly inserted small bore syringe, and greater than the internal diameter of the trailing apical end of the hollow cone at a point best suited for wedge impacting the catheter insertion needle hub when it slip disconnects from the hub of the catheter insertion needle with retraction. Alternative embodiments for prefilled IV catheters and catheters with winged hubs are specified.

4 Claims, 4 Drawing Sheets

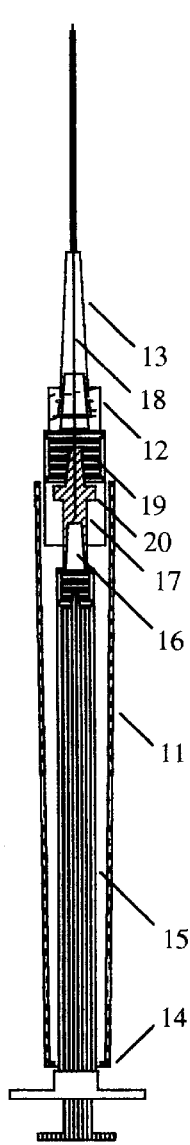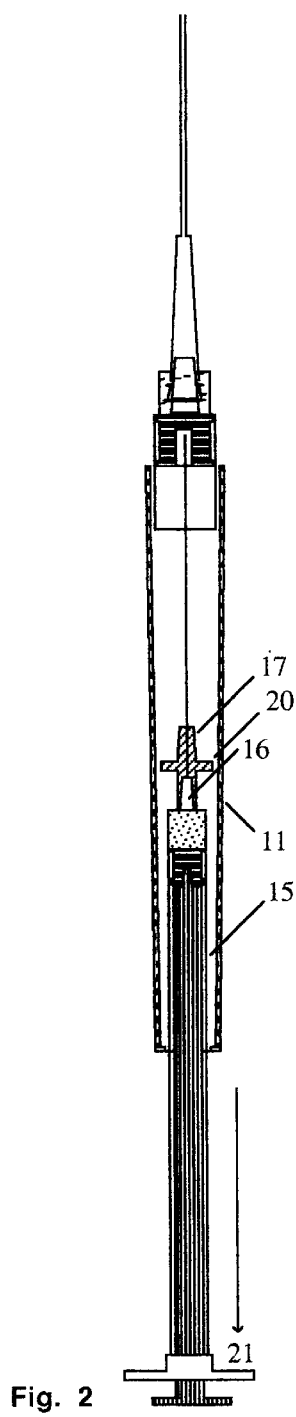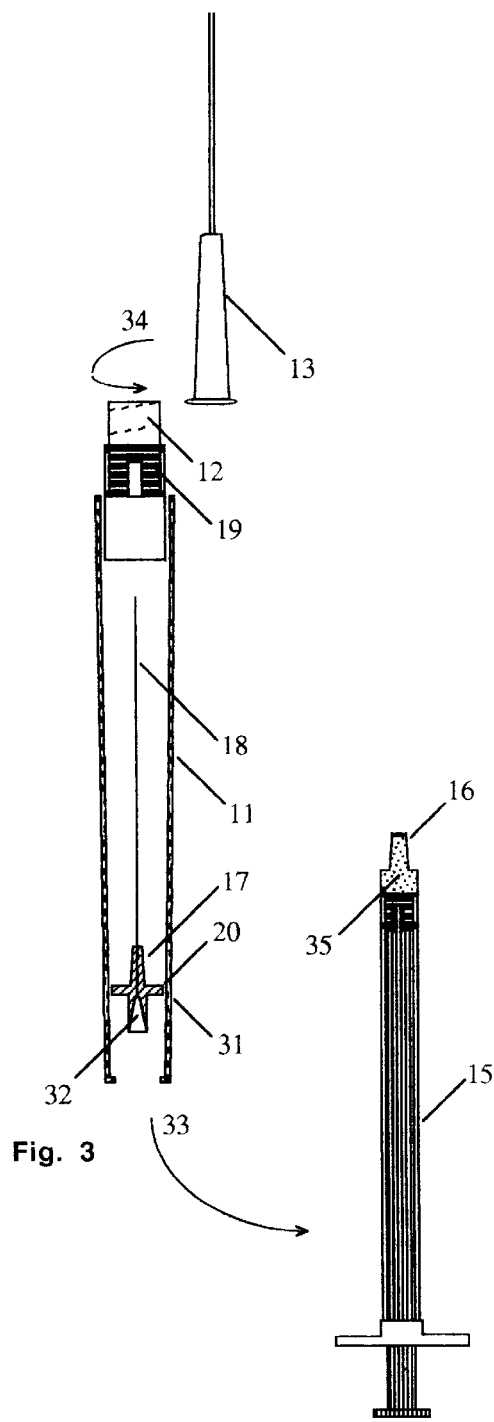
Fig. 1
Fig. 2
Fig. 3

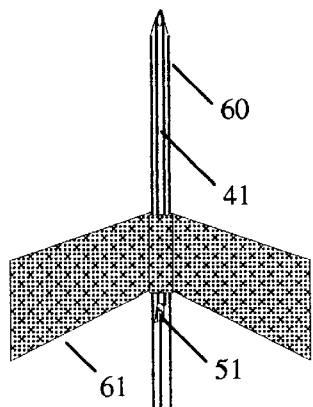
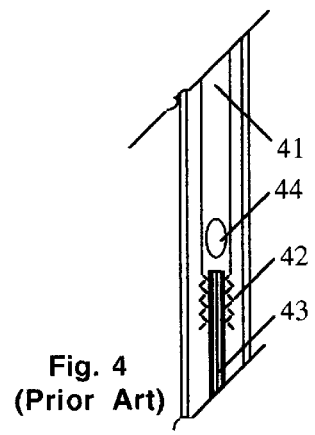
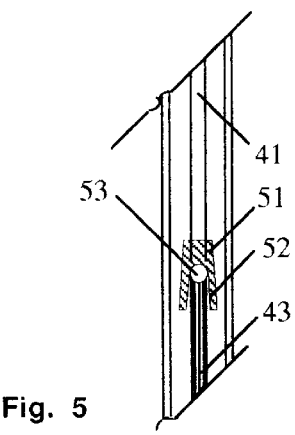
Fig. 4 (Prior Art)
Fig. 5
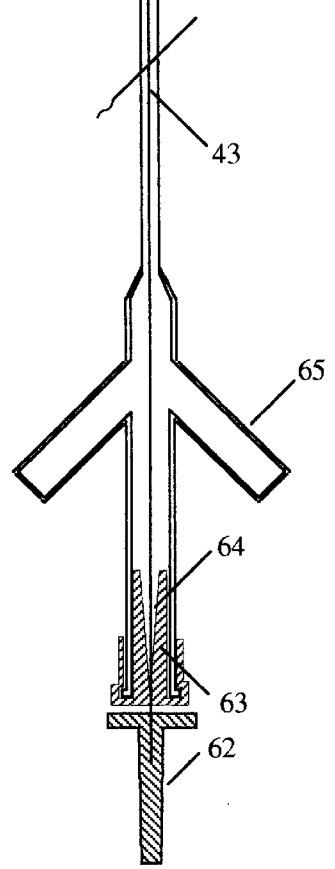
Fig. 6
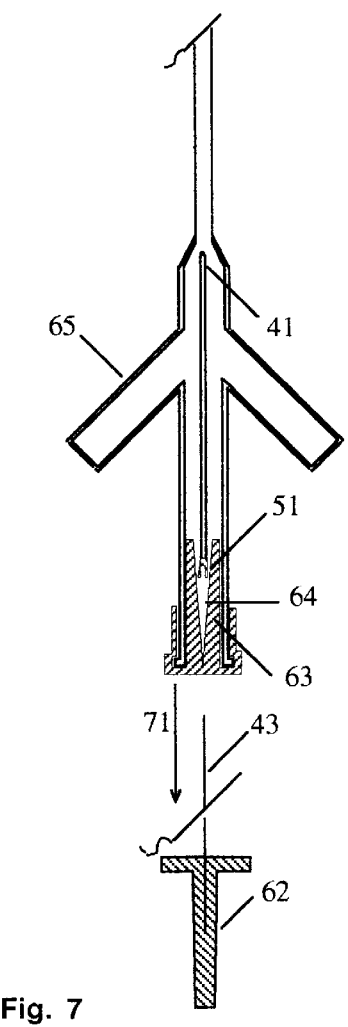
Fig. 7

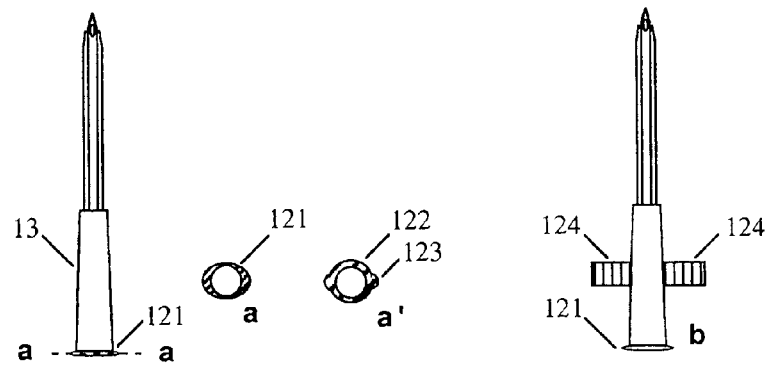
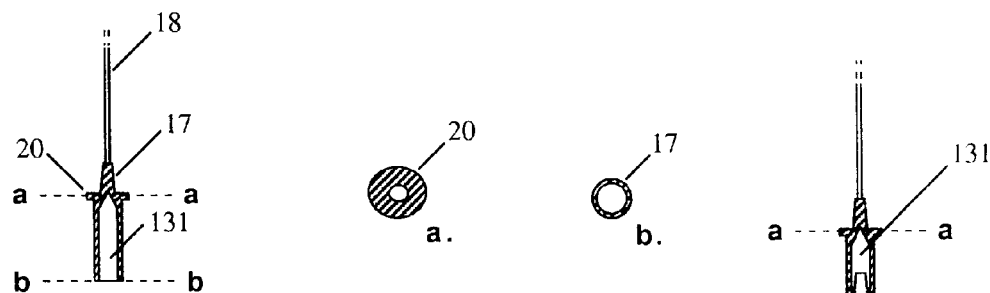
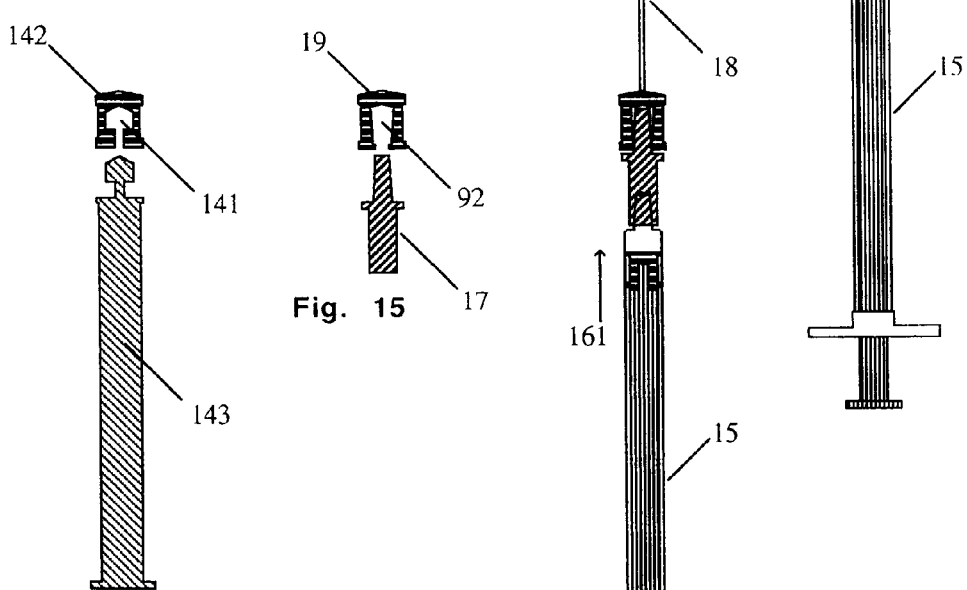
Fig. 12
Fig. 13
Fig. 14
Fig. 15
Fig. 16

SHIELDED IV CATHETER INSERTION ASSEMBLIES

This application claims benefit of provisional appln No. 60/035,362 filed Jan. 10, 1997. This is a continuation in parts with improvements on Shield's U.S. Pat. No. 5,007,901 (Apr. 16, 1991) and U.S. Pat. No. 5,401,250 (Mar. 28, 1995).

BACKGROUND OF THE INVENTION

1. Field of the Invention

An IV catheter insertion device which shields users from accidental needlestick injury from the catheter insertion needle and which protects patients from venous injury during accurate IV catheter placement.

2. Prior Art

In health care settings cross-infection of incurable blood-borne virus infections, including Hepatitis B Virus (HBV), Hepatitis C Virus (HCV), Human Immunodeficiency Virus (HIV), Human T-cell Leukemia Virus (HTLV), and skin-borne antibiotic-resistant bacterial infections, have made it imperative to offer better devices for giving injections and intravenous infusions into patients safely and efficiently. Intravenous silastic catheters have proven extremely useful in hospital settings because, after proper insertion, they may remain in place in a patient for more than a day with minimal venous irritation; and pose no needlestick hazards to health care workers when removed. However, most silastic catheters commonly used in small veins require IV insertion via a hollow-bore steel needle with a sharp beveled tip which is extremely hazardous to users and bystanders and potentially injurious to veins.

Currently, two types of protective devices are commonly used for inserting IV catheters, i.e. devices not filled with infusion fluid before insertion of the catheter and devices filled before insertion of the catheter over-the-needle. Shields' U.S. Pat. No. 5,007,901 (Apr. 16, 1991) applies to both by disclosing an insertion needle guide which breaks away from the trailing end of the insertion needle, such that the entire needle can be trapped during withdrawal into the puncture-resistant housing of the assemby. However, simple specific means for trapping the insertion needle were not clearly specified.

Subsequently, Shields' U.S. Pat. No. 5,401,250 (Mar. 28, 1995) disclosed the use of a hollow cone to wedge impact the hub of a retracted hollow bore steel needle, such that the beveled tip could be safely shielded inside. Further, Shields' U.S. Pat. No. 5,007,901 (Apr. 16, 1991) specified the use of an elastomeric syringe piston for stabilizing the thrust and retraction of the IV catheter insertion needle. However, use of the trailing recess in said piston for manually controlling forward and backward displacement of the hollow-bore steel needle bevel in relation to the leading taper on an IV catheter was not claimed. This innovation, applicable to catheter insertion devices not filled with infusion fluid before insertion of the catheter, remains unclaimed by other inventors. The innovation may prove useful for preventing venous intimal injury, as well as shearing of the catheter by poorly controlled advancement of the needle bevel inside the catheter during the process of IV insertion.

Among competing devices designed for safe user IV catheter insertion via unfilled insertion assemblies, the Critikon PROTECTIV™ and the Becton-Dickinson Insyte™ systems are not structurally comparable because the former depends on a latch mechanism which traps a manually retracted inside-the-catheter insertion needle; and the latter depends on a latched spring mechanism which allows no options for gradually retracting or advancing the insertion needle inside the catheter after IV penetration. Neither is in the best interests of patients, because the former is awkward for users to manipulate between the first and third fingers of the dominant hand with the index finger controlling the relative position of the steel insertion needle; and complications have ensued as a result of catheter shearing by the needle bevel. The latter lacks means for finely adjusting the relationship between the insertion hollow-bore needle bevel and the leading taper in the IV catheter.

Among fluid-filled assemblies, B-D/Deseret currently produce a winged infusion set with a telescoping trailing addition which traps a catheter insertion needle with a vented shank. The instant invention differs in that the catheter insertion needle hub is vented amd trapped by wedge impaction inside the trailing end of the IV catheter insertion assembly.

SUMMARY

The object of this invention is to provide a simple, efficient, easily operated and inexpensive means to accurately insert a silastic IV catheter having a standard flanged hub or a winged hub with minimal risks for accidental needlesticks to users, bystanders and personnel responsible for safe disposal of sharp parts of the IV catheter insertion assembly. A unique feature of the invention, not previously claimed, is the use of the trailing recess in a standard syringe piston for controlling the position of the insertion needle in relation to the taper on the leading end of catheter; and the use of a small-bore tuberculin syringe to do so, as well as to test intracatheter flow by means other than venous blood flash-back. In addition, use of such a syringe permits the safe withdrawal of a small amount of blood for testing immediately after successful catheter placement, if so desired, from assemblies not filled with fluid before insertion of the catheter.

BRIEF DESCRIPTION OF THE DRAWINGS

FIG. 1 is a schematic mid-axial view of the assembly before use in a patient, but after a scabbard for protecting the IV catheter and catheter insertion needle has been removed. Scale is ±1:1 in this view and remaining views, unless otherwise designated.

FIG. 2 is a similar view of the assembly after the IV catheter has been accurately placed; and the insertion needle is partially withdrawn into the bore of the conical housing.

FIG. 3 is a similar view of the assembly after the IV catheter has been accurately placed; the flange on the hub of the IV catheter needle has become wedge impacted in the conical housing with retraction insofar as possible by means of a standard 1.0 mL. disposable syringe; and the IV catheter is left in the vein of a patient.

FIG. 4 is a ±4× enlarged view of prior art venting of the catheter insertion needle and crimping of the trailing end of said needle over a wire used to guide the insertion needle in a winged IV infusion assembly.

FIG. 5 is a ±4× enlarged view of the instant invention which uses a vented catheter insertion needle hub to display venous blood flash-back; and to releasably grasp the leading end of a larger gauge blunt-tipped controlling wire in a similar winged infusion assembly.

FIG. 6 is a foreshortened similar view of an entire, but modified winged IV infusion assembly whose trailing latex stopper is modified to entrap the aforementioned vented catheter insertion needle hub, such that said insertion wire can slip disconnect.

FIG. 7 is a view similar to that in FIG. 6, showing the catheter insertion needle entrapped by means of its vented hub in a conical trap inside said trailing latex stopper, such that the insertion needle and its trailing hub remain in the puncture-resistant housing comprising the trailing end of a winged infusion assembly having two infusion ports.

FIG. 12 shows the catheter hub flange and added details.

FIG. 13 shows catheter insertion needle hub details and fitting specifications.

FIG. 14 shows prior art and piston recess details when the piston is fitted to a standard syringe plunger.

FIG. 15 shows piston recess details when used to control the thrust of a flanged catheter insertion needle hub.

FIG. 16 shows additional piston-insertion needle-small guiding syringe details.

DESCRIPTION OF THE PREFERRED EMBODIMENTS

Figures 8, 9:
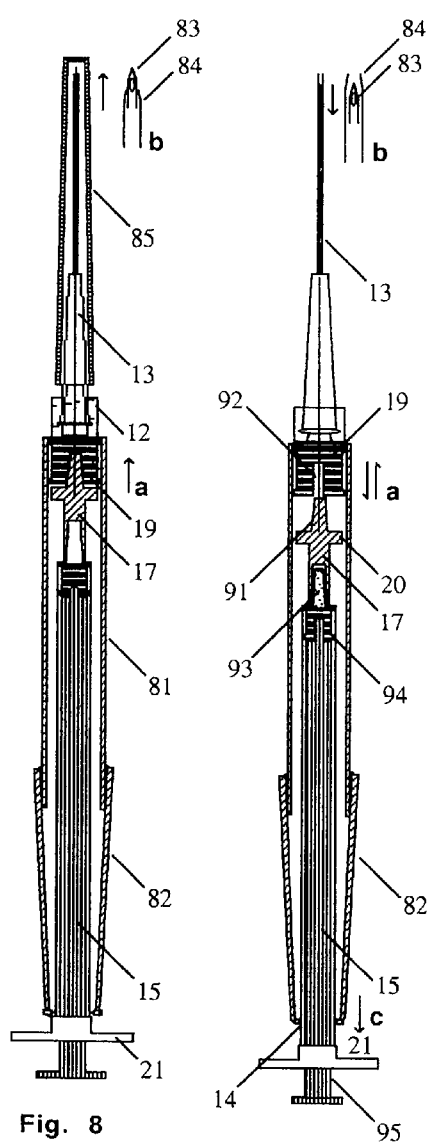
FIG. 8 is a view similar to that in FIG. 1, showing a disposable scabbard for protecting the IV catheter and leading end of the catheter insertion needle on the leading end of the assembly; and the use of a cylindric leading end of the assembly attached to a trailing cone, such that fabrication of the assembly cab be mechanically simplified.
FIG. 9 is a view similar to that in FIGS. 1 and 8, showing the effects of retracting an enclosed syringe on the relationships between its leading slip connection and a recess in a larger syringe piston, such that exposure of the beveled tip of the catheter needle can be reversibly enclosed inside the taper on the leading end of an IV catheter.

The structural features of a preferred embodiment not filled with fluid before use are shown in FIGS. 1–3 and in FIGS. 8–16. Structural features of an embodiment filled with infusion fluid before use are shown in FIGS. 4–7.

FIG. 1 shows a syringe-like hollow cone 11 having a leading frustal end closed by a Luer-Lok 12 used for reversible attachment of the hub of an intravenous catheter 13; and a trailing apical open end 14 through which a small bore Tuberculin syringe 15 slides snugly. The leading end of the small bore syringe has a luer-slip nozzle 16 which reversibly attaches to a trailing recess in the hub 17 of the catheter insertion needle 18. A syringe piston 19 minus the plunger from a syringe of larger bore (such as a standard 3 ml. syringe stabilizes the thrust of the catheter insertion needle 18 which passes through the piston 19; and limits forward motion of the catheter insertion needle hub 17. A circular flange 20 on the catheter needle hub helps control forward motion of the insertion needle 18; and limits backward motion, as shown in FIGS. 2–3.

FIG. 2 shows the catheter insertion needle hub 17 partially retracted into the hollow cone 11 by means of force in the direction of the arrow on the trailing external flange 21 of the small bore syringe 15.

FIG. 3 shows the catheter insertion needle hub 17 retracted as far as possible into the hollow cone 11. Further retraction is stopped at a point of wedge impaction 31 wherein the external diameter of the circular flange 20 on the insertion needle hub 17 becomes equal to or greater than the trailing internal diameter of the hollow cone 11. When the frictional force in the slip connection between the leading luer-slip tip 16 of the small bore syringe 15 and the trailing recess 32 in the catheter insertion needle hub 17 is exceeded, the small bore syringe will break away; and can be safely removed from the cone for further disposition, as indicated by the curved arrow 33. Because the axial length of the hollow cone 11 must be greater than the axial length of the catheter insertion needle 18, the entire needle will be safely trapped and shielded inside the hollow cone 11. The leading catheter 13, then, can be unscrewed from its Luer-Lok connection 12, as indicated by the curved arrow 34; and subsequently be connected to a fluid infusion set, if placement of the IV catheter was accurate. It should be noted, further, that blood leakage from the assembly after catheter placement will be minimal, because the leading end of the hollow cone will be plugged by the large bore syringe piston 19, the trailing end will be plugged by the wedge impacted catheter hub flange 20, and the user can aspirate the contents of the insertion needle 18 into the small bore syringe 15 before it breaks away. A small amount of fluid is depicted at 35 in the small bore syringe, for reasons which will become clear in FIGS. 9–11.

FIG. 4 shows a detail of prior art essential to the use of a hollow bore steel needle for inserting a soft IV catheter on a winged infusion assembly filled with fluid before cannula insertion. The steel needle 41 is crimped 42 onto a guide wire 43 and vented 44 to accommodate venous "flash-back", such that the needle can be retracted after it is certain that the lumen of the needle and the over-the-needle catheter are accurately placed in a vein.

FIG. 5 shows a functionally similar detail in the instant invention wherein the steel needle 41 is fitted with a tiny hub 51 with a trailing recess 52 which slip connects to a guide wire 43 and has a vent 53 distal to the point of slip connection. This alternative form of connecting and venting permits entrapment of the steel inside, instead of outside of the assembly, as shown in FIGS. 6–7.

FIG. 6 shows a soft, over-the-needle catheter 60 enclosing the needle 41 of a winged infusion assembly 61 having a vented hub 51 releasibly attached to the guide wire 43. The guide wire 43 is manipulated by a holder 62 on the trailing end of the assembly whose trailing end is enclosed and accessed by a latex stopper 63 whose interior surface is conical 64 with an open leading frustum and a closed trailing apex. The trailing bulk of the assembly is fitted with two side ports, one of which labeled 65 must be used for filling the assembly and sustaining an IV infusion. The other, not labeled, can be used for intermittent additions of fluids or withdrawing venous blood relatively close to the IV access site, depending on the kind of fittings applied to the port.

FIG. 7 shows the results of manual retraction of the guide wire 43 by means of its holder 62 in the direction of the arrow 71. In short, the steel needle 41 is safely retracted and shielded inside the trailing end of the assembly when its vented hub 51 gets wedge impacted into the conical aperture 64 inside the latex stopper 63. The trailing holder 62 and bulk of the extracted guide wire 43, then become safely disposable, especially if the leading end of the guide wire is blunt and slip connects into the trailing recess 52 in the insertion needle hub 51 properly. The tighter the slip-connection, the further the vented needle hub 51 will be retracted into the conical aperture 64 in the latex stopper 63, before the guide wire 43 breaks away to leave the entire catheter insertion needle 41 securely shielded inside the puncture-resistant housing of the paired infusion ports 65.

FIG. 8 shows additional structural details which simplify the fabrication and extend the usefulness of shielded IV catheter insertion assemblies not filled with fluid before IV insertion. To simplify fabrication, the leading end of a flangeless 3 ml. Luer Lok syringe 81 containing a fitting piston 19 can form the leading end of a catheter insertion assembly whose trailing end is formed by a hollow cone 82 whose frustum is permanently bonded over the trailing end of said flangeless syringe after a 1 ml. Tuberculin syringe 15 releasibly slip-connected to the catheter insertion needle hub 17 has been inserted through the trailing open apex such that the insertion needle hub 17 is advanced forward as far as possible, as shown by the arrow at a; and the insertion needle bevel 83 is advanced as far as possible through the leading taper 84 in the IV catheter 13 releasibly attached to the Luer-Lok 12 in said syringe, as shown by the arrow at b. During assembly a disposable scabbard 85 should be added over the catheteer 13. To further simplify fabrication, the flange 21 on the Tuberculin syringe 15 might be added after assembly of preceding parts.

FIG. 9 illustrates a unique feature of the assembly in that the insertion needle bevel 83 can be retracted inside the leading taper 84 of the IV catheter 13, as shown at b, by appropriate retraction of the external flange 21 on the 1 ml. Tuberculin syringe 15 in the direction of the arrow shown at c. The fit of the leading taper 91 on the catheter insertion needle hub 17 into the recess 92 in the trailing end of the large bore syringe piston 19 can be adjusted to palpably as well as visibly facilitate forward and backward movement of the leading Tuberculin syringe taper 91 within the axial length of the piston recess 92 as depicted by the arrows at a. A good fit will be assured by making the leading diameter of the taper 91 slightly larger than the opening diameter of the of the recess 92 in the piston 19, such that the elastic material of the piston must stretch slightly to restrict insertion and will grasp the taper after insertion to a depth limited by the recess 92 in the piston 19 or the circular flange 20 on the insertion needle hub 17. These relationships are illustrated by comparing the outline of the recess with that of the leading hub taper in FIGS. 1,2,3,8,9,10 and 11. This unique feature, along with a snug fit of the tuberculin syringe 15 through the trailing apical aperture 14 of the cone 82, enables the user to reversibly retract and extend the needle bevel 83 a critical distance in relation to the leading catheter taper 84, such that the catheter can be advanced through a vein without exposing a sharp protruding needle bevel capable of passing through the wall of the selected vein or causing intimal injury. Moreover, the critical distance being equal to the depth of the recess 92 in the piston 19, shearing of the catheter becomes unlikely because insufficient length of catheter to allow bending will lie beyond the needle bevel 83 during catheter advancement.

Figure 10:
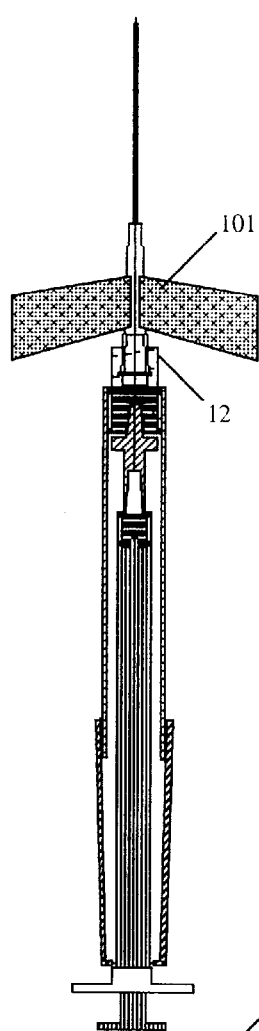
FIG. 10 is a view similar to that in FIGS. 1 and 8, showing the use of an IV catheter with a winged, as well as a terminally flanged hub for safely infusing fluids into small veins.

FIG. 9 shows an additional feature, labeled 35 in FIG. 3, unlabeled in FIGS. 2 and 10, and labeled 93 to signify a small amount of blood in the bore of the leading taper or in leading end of the tuberculin syringe 15. This show of visible blood, called "flash-back" in the leading taper 93, as well as in a transparent catheter insertion needle hub 17, usually signifies accurate venous entry of the needle bevel 83 and the taper 84 on the leading end of the catheter 13. However, the use of a Tuberculin syringe 15 having its own piston 94 and attached plunger 95, enables the user to manipulatively check accuracy of IV catheter insertion and flow character at all stages of insertion after observation of initial "flash-back"; and, if desired, safely withdraw a small quantity of undiluted fresh venous blood for testing.

Figure 11:
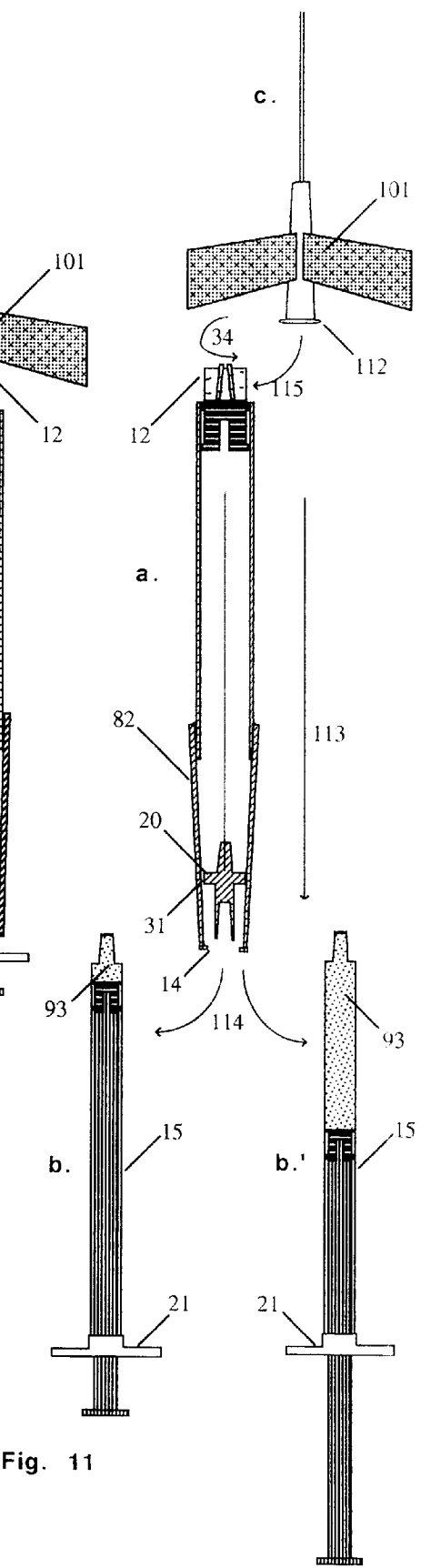
FIG. 11 is a view similar to that FIG. 10, showing the sequential disposition of components after the winged IV catheter is accurately placed; and the utiltity of a 1.0 mL. disposable syringe for simultaneously collecting a small quantity of undiluted fresh blood for testing before the trailing end of the catheter hub is attached to an infusion reservoir.

FIGS. 10–11 recapitulate sequential positions of parts in the IV catheter insertion assembly, using a winged infusion modification of the catheter hub 101 having trailing flanges 112 for reversible attachment to the leading Luer-Lok 12. FIG. 10 shows the assembly ready for intravenous insertion with a leading needle scabbard (not shown) removed, and no blood in the assembly. FIG. 11 shows sequential positions of parts just before and after successful placement of the IV catheter with a winged hub 101.

In sequence:

a. the tuberculin syringe 15 is withdrawn by means of its trailing flange 21 in the direction of the arrow 113 until the circular flange 20 on the catheter insertion needle hub becomes wedge impacted 31 in the trailing apical end of the hollow cone 82.

b. further retraction in the same direction will cause the Tuberculin syringe 15 to break away and exit, as indicated by the arrows at 114. The Tuberculin syringe 15 will exit variably filled with blood 93, as indicated at b. and b.', depending on the choices of the users for withdrawing blood samples vs. emptying the syringe and catheter needle before retraction.

c. counter-clockwise rotation of the leading end of the assembly depicted by curved arrow at 34 will allow the separated IV catheter with a winged hub 101 to remain in place, as the remains of the assembly are displaced, as indicated by the arrow at 115.

FIGS. 12–16 show hub and piston details which are common in the prior art, but require minor adjustments to work optimally in this shielded IV catheter insertion assembly. FIG. 12 shows the catheter hub 13 with a circular trailing flange 121. When cross-sectioned at a—a, it will be noted that the circular trailing flange 121 is eccentric on each side, as shown in a, with a constant apogee diameter of ±7.76 mm.; and an perigee diameter which varies in needles made by different manufacturers. Alternatively, as shown at a', the flange 122 is round, but extra flanges 123 are appended on each side to yield a maximal transverse diameter of ±7.76 mm. Such trailing flange deviations from being perfectly round are essential to the reversible attachment of standard IV catheters and standard hollow bore steel needles to standard Luer-Loks on leading ends of syringes or leading connectors on IV infusion sets. As shown at b, IV infusion catheters, are sometimes made with auxiliary wing-like flanges 124 appended substantially ahead of the trailing flanges 121 in order to facilitate finger manipulation of the catheter after retraction of the catheter insertion needle and to provide secure taping to the skin overlying a selected vein. Here, a small flange 124 is shown appended on each side in order to prevent rotation of the catheter hub when the Luer-Lok is rotated counter-clockwise to disengage the catheter hub, as shown in FIGS. 3 and 11. It should be noted, further, that addition of wings 101 on the catheter hub, as shown in FIGS. 10–11, accomplishes the same purpose.

FIG. 13 shows the catheter insertion needle hub 17 with the leading part of the insertion needle 18 cut off. This type of hub with variations in the form and size of the flange shown at 20 is characteristic in IV catheter placement assemblies lacking shields for protecting the catheter insertion needle after use; and which depend on direct manual operation of the needle hub to insert the catheter; or, alternatively, attachment to a standard syringe with or without a Luer-Lok for guiding insertion. Characteristically, such insertion needle hubs are optically transparent and made with large recessed chambers 131 for observing venous blood "flash-back" from the leading end of the catheter insertion needle 18 after accurate intravenous insertion.

Modifications essential to efficient use in this unfilled IV catheter insertion assembly are:

a. the external diameter of the circular flange 20, cross-sectioned at a—a, must be more than the external diameter of the small bore syringe used to guide insertion; less than the internal diameter of the leading end of the hollow cone; and more than that in the trailing end of the hollow cone adapted to wedge impact this circular flange 20, as shown in FIGS. 3 and 11. Because standard 3.0 ml. cylindric syringes produced by different manufacturers vary in internal bore from a diameter of ±8.66 to 9.10 mm., larger bore syringes can vary more, and the internal diameters of cylindric syringes inserted into hollow cones, as depicted in FIG. 8, can vary even more in differing parts, it is not possible to be more specific concerning the precise optimal external diameter of said circular flange 20.

b. the inside configuration of the trailing end of the catheter insertion needle hub 17, cross-sectioned at b—b, is characteristically standard in that it lacks external flanges, and is uniformly adapted internally to accept a syringe nozzle to comprise a reversible standard luer-slip connection, as shown in FIGS. 1,2,8,9, 10.

c. However, as shown at c. (to the right) where the arrow indicates the direction of insertion of the leading luer slip connector on a standard tuberculin syringe 15, the depth of the recessed chamber 131 can vary to display more or less venous blood "flash-back", before the syringe is used to assess accuracy of catheter insertion, as previously described.

FIG. 14 shows how a configured recess 141 in the trailing end of a standard syringe piston 142 is normally configured to irreversibly grasp the leading end of an inserted syringe plunger 143. The piston elastomer compresses and bends enough to allow insertion of the plunger tip, but does not stretch or bend enough to allow extraction when both are axially aligned inside a syringe.

FIG. 15 shows how the configuration of the recess 92 in a plungerless syringe piston 19 can be altered to reversibly accept and release the leading end of a catheter insertion needle hub 17, such that resistance to hub entry and hub extraction can be finely adjusted, as described with FIG. 9 and illustrated further, using an arrow 161 in FIG. 16. With good adjustment, the user should be able to feel, as well as see,when the leading end of the catheter insertion needle hub slides in and pops out, because the leading end of the catheter needle hub 17 is slightly larger than the trailing opening of the aperture 92 in an elastomer capable of stretching and recoiling under properly aligned pressures. It should be mentioned, further, that elastomeric syringe pistons are characteristically made with leading and trailing ends of greater external diameter than the internal diameter of the cylindric syringe bore, such that the pistons are compressed and prevent leakage into the trailing bore of the syringe during activation. However, when the piston is not connected to a securely attached plunger the piston will neither rotate nor displace backward because a relatively large area of frictional contact between the piston and syringe bore resists displacement. Thus, in this assembly, the piston will not move backwards significantly if the elastomer to catheter insertion needle hub taper are optimally co-adjusted. Moreover, being housed in the frustum of a hollow cone 11, 82 whose bore progressively decreases toward the apex, the piston can not be expected to retract sufficiently toward the apex to interfere with the usefulness of the assembly.

In use of this unfilled assembly, as specified, the user sequentially:

1. Carefully selects a vein to be catheterized.
2. Properly prepares and sterilizes the overlying skin.
3. Puts on a proximal tourniquet.
4. Takes the assembly out of its sterile package (not shown) and removes the disposable needle scabbard 85.
5. Inserts the leading needle bevel 83 and taper 84 of the catheter 13 through the skin subcutaneous tissue and wall of the selected vein, more or less like he/she would do, using an ordinary hollow bore steel needle attached to a syringe with a leading Luer-Lok.
6. When "flash-back" of venous blood is observed into the recess 131 of catheter insertion needle hub 17, or into the tapered nozzle 91 of the Tuberculin syringe, the user advances a little further by combinations of feeling, experience and observation of continued "flash-back to be sure that lumen of the vein has been accessed.
7. The user, then, pulls back on the trailing flange 21 of the Tuberculin syringe 15 to recess the bevel 83 of the insertion needle 18 into the taper 84 of the catheter 13, as shown in FIG. 9.
8. Continuing to feel and observe "flash-back", the user advances the catheter up through the lumen of the vein without touching the trailing flange 21 on the Tuberculin syringe, until the catheter 13 is fully inserted, such that only the hub remains visible.
9. If there is any question about position or patency during this advancement, the user may activate the plunger 95 in the trailing end of the Tuberculin syringe 15 to aspirate blood or flush blood forward.
10. When the catheter 13 is fully inserted, the user should activate the plunger 95 again, or for the first time, to be sure of accurate positioning and patency with the venous lumen.
11. If the user chooses to withdraw a small sample of undiluted venous blood for testing, the tuberculin syringe should be one-half to two-thirds filled at this time. If the user doesn't want a sample, the contents of the Tuberculin syringe can be flushed back into the vein.
12. The catheter having been successfully placed, the user withdraws the Tuberculin syringe by means of its trailing flanges 21, as shown in FIG. 11. When the retraction of the tuberculin syringe is temporarily stopped by the initiation of a wedge impaction 31 of the circular flange 20 on the insertion needle hub 17 into the apex of the hollow cone 11,82, the user should flush the remaining contents of the Tuberculin syringe 15 and the catheter insertion needle 18 into the lumen of the hollow cone 11,82, if he/she doesn't want to obtain a venous blood sample for testing.
13. The tourniquet, if one was applied, should be removed from the patient.
14. The Tuberculin syringe 15 should be completely extracted by further traction on its trailing flanges 21 and, then, be safely disposed when convenient.
15. A sterile pledget (not shown) should be placed over the venipuncture site.
16. With finger pressure from the user's non-dominant hand over the pledget and catheter hub 13 to prevent venous bleeding and to prevent rotation and backward movement of the catheter, the remaining parts of the catheter insertion assembly should be screwed off the trailing flanges 121 of the catheter hub originally attached to the leading Luer-Lok 12 on the leading end of the hollow cone 11.
17. The dominant hand, customarily used for inserting the assembly and leading catheter should dispose of the enclosed and shielded catheter insertion needle, while the non-dominant hand is used to maintain pressure over the venipuncture site long enough to preclude venous bleeding and oozing, preferably with elevation of the patient's arm or hand to reduce venous pressure.

18. Finally, the leading end of an IV infusion set should be securely attached to the trailing end of the catheter hub by means of a Luer-Lok or a Luer-slip connector.

When using a filled version of this assembly 65, the sequential procedure is fundamentally similar, but differs in that a winged catheter hub 61 is usually used to insert the catheter 60 over a catheter insertion needle 41 which is guided by a retractible wire 43 which breaks away from a vented 53 catheter insertion needle hub 51 to become trapped and shielded in the trailing stopper 64 of the assembly with retraction of the guide wire. Thus, the user is obliged to gauge accuracy of catheter insertion by feel, experience, observing the patterns of venous blood "flashback" through the insertion needle hub vent 53, and testing if flow from a pre-attached infusion set is patent. After successful catheter insertion, only the retracted guide wire is detached, and needs to be discarded safely.

The unique structural features of this invention are the disclosure of a catheter insertion needle hub which breaks away from its proximal guide, when wedge impacted into hollow conical trap which leaves the insertion needle safely shielded inside the assembly; the use of a small bore syringe, such as Tuberculin syringe, as a shielded catheter insertion needle guide; and the use of a syringe piston to delicately control the thrust of the catheter insertion needle with respect to a leading taper on the catheter. The embodiments, as specified, are exemplary only and not intended to be limiting. It will be appreciated by those skilled in the art that wide variation in details can be made without departing from the spirit of the invention as hereinafter claimed.

What I claim is:

1. A shielded IV catheter insertion assembly for safely inserting an intravenous catheter into a selected vein of a patient, the assembly comprising:

(a) a silastic catheter having a leading taper, a tubular body and an eccentrically flanged trailing hub reversibly attached to a Luer-Lok connector on the closed leading end of (b) a puncture-resistant holder having a hollow conical body containing a first elastomeric syringe piston in the leading frustum, a trailing apical aperture diameter and an axial length substantially equal to the external diameter and axial length of the barrel of (c) an axially inserted small bore syringe having trailing external flanges, a contained second elastomeric piston activated by a flanged plunger and a tapered nozzle slip-connected to the inside of the receptive hub of (d) a catheter insertion needle having a leading sharp bevel, a hollow shank longer than said tubular body of the silastic catheter and a circular flange on the outside of the needle hub whose external diameter is substantially greater than the inside diameter of said trailing apical aperture in said puncture-resistant holder;

the assembly being constructed such that said axially inserted small bore syringe serves (i) as a guide which reversibly controls the thrust of the catheter insertion needle through said first elastomeric syringe piston, through said Luer-Lok connector and through said tubular body of the silastic catheter, (ii) which reversibly impels venous blood flow through the catheter insertion needle and (iii) later serves as a guide which breaks away from said slip-connected receptive hub of the catheter insertion needle to leave the entire catheter insertion needle safely shielded inside said puncture-resistant holder after sufficient traction is applied to said trailing flanges on the small syringe to cause a wedge impaction of said circular flange on said receptive hub of the catheter insertion needle in the trailing apical end of said hollow conical body of said puncture-resistant holder; and finally such that, after rotating said puncture-resistant holder to release said eccentrically flanged trailing hub of the silastic catheter from said Luer-Lok connector on said closed leading end of the puncture-resistant holder, the contained shielded catheter insertion needle can be disposed of separately and safely.

2. The shielded IV catheter insertion assembly as in claim 1 wherein said first elastomeric syringe piston is made with a trailing aperture whose opening is slightly smaller in diameter than the leading end of said tapered nozzle on the small bore syringe and whose depth is almost equal to the length of said sharp bevel on the leading end of the catheter insertion needle, such that the silastic catheter can be controllably advanced in a patient's vein with or without said sharp bevel protruding beyond said leading taper in the silastic catheter.

3. The shielded IV catheter insertion assembly as in claim 1 wherein said eccentrically flanged trailing hub on the silastic catheter in a preferred alternative embodiment has attached wings to increase surface area for finger stabilization and for taping to a patient's skin overlying the selected vein after the silastic catheter is inserted accurately.

4. The shielded IV catheter insertion assembly as in claim 1 wherein the puncture-resistant holder may be fabricated conveniently in two parts, for example:

(a) a leading standard 3 mL. Luer-Lok syringe of uniform cylindric bore containing said first piston without a plunger in the leading end and lacking trailing external flanges for finger placement on the trailing end of the syringe barrel; and (b) a trailing hollow cone whose leading open frustum, after slip-connection of the catheter insertion needle with the small bore syringe, such as a 1.0 mL. Tuberculin syringe, and axial insertion of both, is permanently attached over the flangeless trailing end of said syringe barrel, the combined length of the cylindric barrel and said hollow cone becoming approximately equal to the length of said barrel on said Tuberculin syringe and the internal diameter of the trailing apex of said hollow cone being almost equal to the external diameter of said barrel of said Tuberculin syringe, such that said circular flange on the outside of said catheter needle hub will become wedge impacted in said trailing hollow cone in appropriate position to retain and shield the entire catheter insertion needle within the combined cylindric/conical bore after complete retraction of said Tuberculin syringe with breakage of said slip-connection to said receptive hub on the catheter insertion needle.

* * * * *